United States Patent [19]

McDonald

[11] Patent Number: 4,883,049
[45] Date of Patent: Nov. 28, 1989

[54] APPARATUS FOR USE IN REFILLING AN ANESTHETIC VAPORIZER

[75] Inventor: Sandy McDonald, Barrie, Canada
[73] Assignee: Southmedic Incorporated, Barrie, Canada
[21] Appl. No.: 154,444
[22] Filed: Feb. 5, 1988

Related U.S. Application Data

[63] Continuation of Ser. No. 873,954, Jun. 13, 1989, abandoned.

[51] Int. Cl.$^4$ .............................................. A61M 17/00
[52] U.S. Cl. .......................... 128/202.22; 128/202.27; 128/203.12
[58] Field of Search ....................... 128/200.14, 204.14, 128/204.18, 205.24, 674, 202.22, 202.27, 203.12, 203.19; 251/149.6; 285/401; 141/15, 97, 349, 348; 222/74

[56] References Cited

U.S. PATENT DOCUMENTS

| | | | |
|---|---|---|---|
| 2,310,021 | 2/1943 | Heidrink | 128/201.18 |
| 3,021,840 | 2/1962 | Hallamore et al. | 128/201.14 |
| 3,170,667 | 2/1965 | Szohatzky | 251/149.6 |
| 3,351,089 | 11/1967 | Garrahan | 125/205.21 |
| 3,441,046 | 4/1968 | Cranage | 251/149.6 |
| 3,448,760 | 6/1969 | Cranage | 251/149.6 |
| 3,512,800 | 5/1976 | Romney et al. | 285/401 |
| 3,544,257 | 12/1970 | Cranage | 251/149.6 |
| 4,072,146 | 2/1978 | Howes | 128/674 |

FOREIGN PATENT DOCUMENTS

| | | | |
|---|---|---|---|
| 1193241 | 5/1970 | United Kingdom . | |
| 2189472 | 10/1987 | United Kingdom | 128/910 |

Primary Examiner—Max Hindenburg
Assistant Examiner—K. M. Reichle
Attorney, Agent, or Firm—Bauer & Schaffer

[57] ABSTRACT

The invention provides an apparatus to retrofit existing anesthetic vaporizer canisters; said apparatus being adapted to be installed in the refill opening of a standard vaporizer canister and configured so that only one specifically assigned refill key index can be used to refill the canister in order to ensure that anesthetics are not inadvertently mixed or substituted in specifically designated vaporizer canisters.

8 Claims, 4 Drawing Sheets

APPARATUS FOR USE IN REFILLING AN ANESTHETIC VAPORIZER

This is a continuation of Ser. No. 873,954 filed June 13, 1986, now abandoned.

The present invention relates to an adapter for use with an anesthetic vaporizer and a refill key index therefor.

BACKGROUND OF INVENTION

It is common practice for two or three anesthetic vaporizer canisters to be maintained in side-by-side relationship on a mobile or stationary rack. Each of these anesthetic vaporizer canisters is charged with a different anesthetic. Located on the side of each canister is a refill means comprised of an integrally molded funnel terminating at an internally threaded fluid inlet opening into the interior of the canister. A stopper having a threaded base designed to engage the internal threads of the opening is provided in order to seal the canister.

To refill an anesthetic vaporizer canister, the threadably secured stopper is removed from the fluid inlet of the refill funnel and the liquid anesthetic is poured into the refill funnel and thence into the vaporizer canister. In order to prevent a mixture of different types of anesthetics in the same vaporizer canister, or to prevent the substitution of one type of anesthetic for another, a colour coding system is used, with each anesthetic canister and refill container being clearly marked with its distinguishing colour.

In order to further minimize the possibility of error particularly where several professionals share the same anesthetic equipment the refill key index described herein has been created.

OBJECTS OF INVENTION

It is a primary object of the present invention to overcome the inadequacies of the present refill practice for anesthetic vaporizers by providing a means to retrofit existing anesthetic vaporizer canisters with an adapter capable of functioning with a refill key index.

A principal object of the present invention is to provide an adapter for use with a standard anesthetic vaporizer canister having a fluid refill inlet, the adapter including a refill key index having a dispensing key containing a fluid discharge outlet, said adapter comprising body means adapted to be removably secured in the refill inlet of a standard anesthetic vaporizer canister. The said body means is provided with a guide means for receiving the dispensing key of a refill key index. There is further provided a selector means in said guide means adapted to selectively receive a specifically configured dispensing key of a refill key index. A bore is provided in said body means for transmitting a fluid from the discharge outlet of a refill key index through the adapter to the anesthetic vaporizer canister. A positioning means located in the guide means if provided to align the fluid discharge outlet of the dispensing key with the central bore means of the adapter when the dispensing key is inserted into the guide means.

These and other features of the invention will now be described with reference to the following drawings wherein a preferred embodiment of the invention is illustrated in which.

DETAILED DESCRIPTION OF THE DRAWINGS

Figure 1:
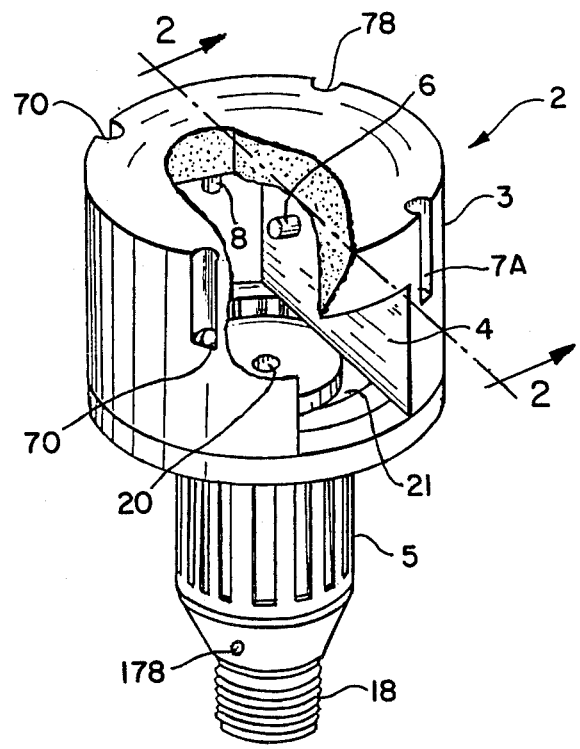
FIG. 1 is a side elevational view in partial section of the adapter according to the present invention.

Detailed reference will now be made to the drawings wherein like reference numerals will identify like parts.

Figure 3:
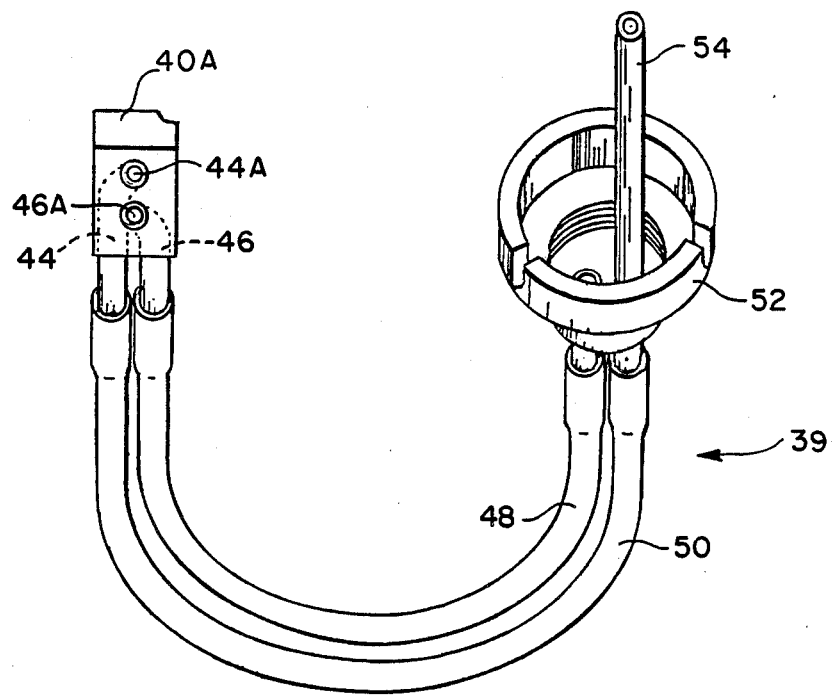
FIG. 3 is a perspective view of a refill key index.

Referring to FIG. 3, a refill key index 39, is comprised of a cap member 52 adapted to engage a bottle of liquid anesthetic (not illustrated), a pair of flexible hoses 48 and 50 extending from one end of cap 52 to a refill key 40 containing a liquid discharge outlet 46A and an air inlet opening 44A. It will be seen that the ends of the two hoses 48 and 50 opposite the cap 52 communicate with channels 44 and 46 respectively in the body of the dispensing key 40 and terminate at the fluid outlet 46A and air inlet 44A respectively. Hose member 48 is adapted to deliver liquid anesthetic to the discharge outlet 46A of the refill key index 39, while hose member 50 is adapted to transfer air into a bottle of liquid anesthetic during the refill operation in order to prevent an interruption of the flow of anesthetic and the formation of a vacuum inside the bottle of anesthetic. There is further provided an extension 54 on the air hose 50, said extension 54 projecting outwardly from the interior of the cap 52 to ensure that incoming air is delivered above the liquid discharge opening in the bottle when it is inverted in accordance with the refill practice as will be described hereinafter.

Figure 4:
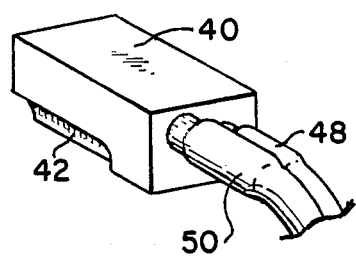
FIGS. 4, 5 and 6 are perspective views of three dispensing keys of the refill key index.
Figure 5:
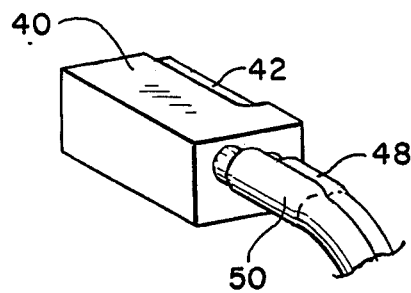
Figure 6:
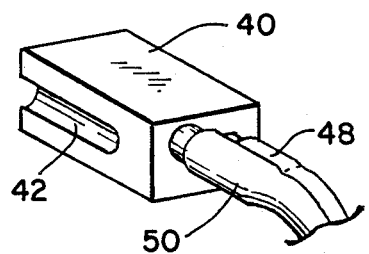

In FIG. 4, there is shown a dispensing key 40 with a detent 42 located on an outside surface. The position of the detent 42 on a particular dispensing key 40 will be unique for each specific anesthetic. Two other examples of locations for detent 42 are shown in FIGS. 5 and 6.

Figure 7:
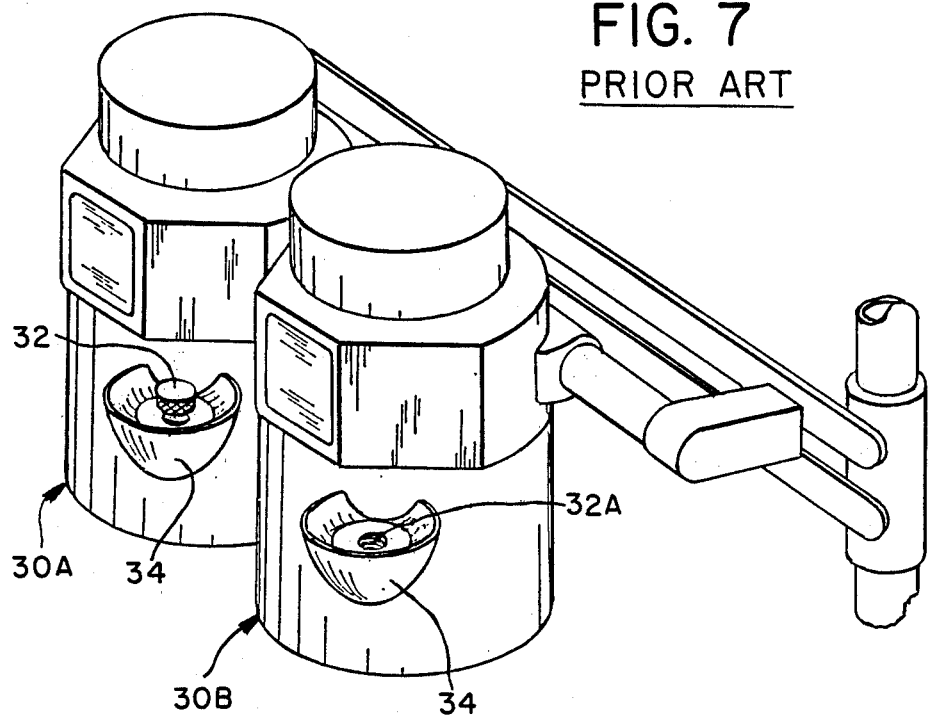
FIG. 7 is a perspective of a pair of vaporizer canisters.

Referring to FIG. 7, there is illustrated a pair of standard anesthetic vaporizer canisters 30A and 30B, each of which is shown to have a refill means comprised of an integrally molded funnel 34 located on the lower portion of the exterior wall, said funnel 34 having unitary inwardly sloping side walls terminating at an internally threaded opening 32A communicating with the interior of the canister. There is further provided a sealing plug 32 adapted to threadably engage the threads of the opening 32A in order to seal the canister 30A or 30B.

In FIG. 1, an adapter 2 according to the invention is shown to be comprised of two cylindrical body portions, an upper body 3 and a lower body 5; the lower body 5 is about one half the diameter of the upper body 3. The two body portions 3 and 5 are maintained together as a unit by four screws 7A,7B,7C, and 7D. The upper body 3 is provided with a guide channel 4 adapted to receive a dispensing key 40 of a refill key index 39, said guide channel 4 characterized as a rectangular opening of uniform cross section, open at both ends, and formed centrally and horizontally in body portion 3.

Figure 2:
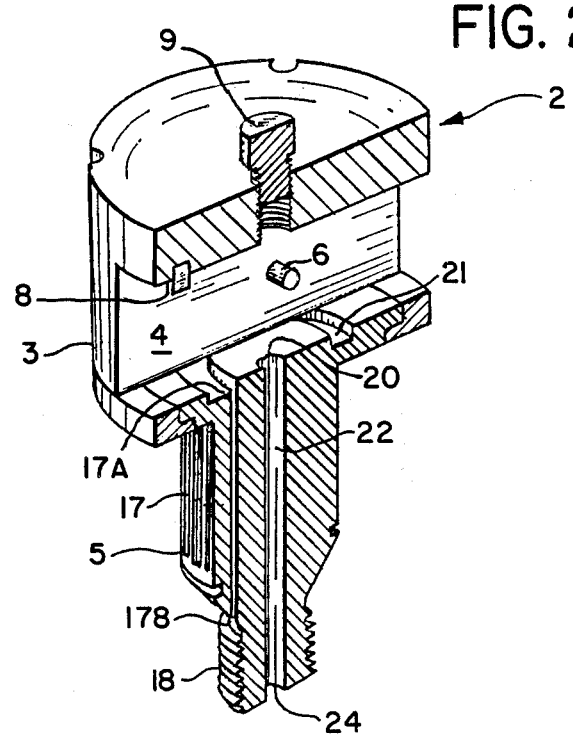
FIG. 2 is a central vertical section taken along line 2—2 of FIG. 1.

In FIG. 2, which is a sectional view of the aapter 2, it will be seen that in the interior of the lower body portion 5 there is provided a bore 22 communicating at 20 with the lower horizontal surface of the guide channel 4, and with the base of the adapter 2 at opening 24.

There is also provided in body member 5 at least one air inlet channel 17 that communicates at opening 17A at one end with a duct 21 formed in the floor of the central opening 4 and at the other end with the exterior at 17B. Also shown in figure 2 is a retaining member 9, which is a thumb screw adapted to releasably secure a dispensing key 40 of a refill key index 39 during the refilling procedure. A few turns of the retaining member 9 will ensure that the refill key index 39 cannot be inadvertantly removed from the adapter 2.

Referring to FIGS. 1 and 2 it will be seen that within the area defined by the guide channel 4 is an alignment member 8 which is illustrated as being a small rod like member positioned at the rear of the guide channel 4. Thus, when the dispensing key 40 of the refill key index 39 is inserted into the guide channel 4, the alignment member 8 abuts the leading surface 40A of the dispensing key 40, thereby arresting the forward movement of the dispensing key 40 at a point where the fluid discharge opening 46A of the dispensing key 40 and the opening 20 in the floor of the guide channel 4 are aligned, thereby providing access to the interior of the canister 31A or 31B through the central bore 22. Hence, a conduit for passage of the liquid anesthetic into the interior of a vaporizer canister is created when the adapter unit 2 is installed and the refill key index 39 is properly inserted into the guide channel 4.

Referring to FIGS. 1 and 2, there is further provided a selector 6 which is a uniformly shaped cylindrical member, positioned on an interior wall of the channel 4. The placement of the selector 6, and the configuration of the detent 42 on the dispensing key 40 of a refill key index 39 must correspond if a functional entry into the guide channel 4 is to be achieved by the refill key 40. The representation of the selector 6 in FIG. 1 is an example and is not intended as a restriction on the invention with reference to the number of or position of selectors 6. The position of selector 6 in FIGS. 1 and 2, for example will engage in detent 42 of key 40 illustrated in FIG. 6. The selector 6 may consist of at least one rod shaped member extending into the channel 4 and in the case where there are two or more vaporizer canisters 31A and 31B equipped with an adapter 2, in side-by-side relationship, the selector 6 will be uniquely placed for each anesthetic vaporizer.

A further feature of the adapter 2 illustrated in FIG. 1 is the threaded connector 18, which is used to securely maintain the adapter 2 in an anesthetic vaporizer canister 30A or 30B. The thread pattern of the connector 18 is such that it can engage the threads of the refill opening 32A normally occupied by the plug member 32 of the refill funnel 34 of a standard anesthetic vaporizer 30A or 30B.

Figure 9:
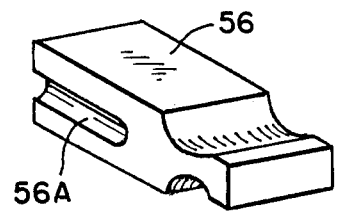
FIG. 9 is a perspective of a sealing plug for use with the adapter and appears on the sheet of drawings bearing FIG. 4, 5, & 6.

In FIG. 9, there is illustrated a sealing plug 56 which is inserted into guide channel 4 of the adapter 2 in order to seal an anesthetic vaporizer 31A or 31B that has been equipped with the adapter unit 2, in order to prevent evaporation of the anesthetic from the canister. In order for the sealing plug 56 to be inserted into the guide channel 4, it is necessary for the plug 56 to be configured with a detent 56A that will cooperate with selector 6 of the host adapter 2.

Figure 8:
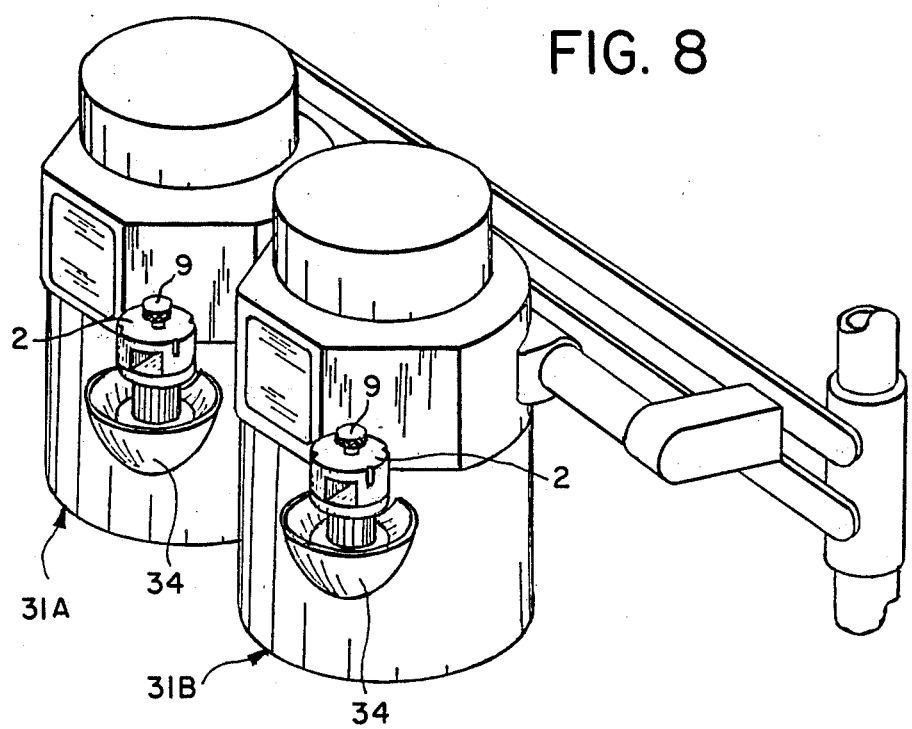
FIG. 8 is a perspective of a pair of vaporizer canisters having the adapter of the present invention installed.

In order to take advantage of the invention, the stopper 32 of the refill funnel 34 of a standard vaporizer canister 30A or 30B is removed and the adapter 2 of the present invention is then installed by threadably engaging the threaded connector means 18 in the opening 32A. With the adapter 2 securely installed in a vaporizer canister 31A or 31B as illustrated in FIG. 8, a refill key index 39 is secured on a designated bottle of liquid anesthetic. The dispensing key 40 of the refill key index 39 is inserted into the guide channel 4 of the adapter 2 until the leading surface 40A of the dispensing key 40 abuts the alignment member 8. The fluid outlet 46A of the refill key 40 and the opening 20 in the floor of the guide channel 4 will now be aligned. Simultaneously the air inlet opening 44A of the dispensing key 40 and the duct 21 will also be aligned thereby providing a passage for the free flow of air into the bottle of liquid anesthetic in response to the flow of anesthetic into the vaporizer canister. The retaining member 9 is turned so that it exerts pressure on the dispensing key 40, thus ensuring that the refill key index 39 cannot be inadvertantly removed from the adapter 2, as well as ensuring that a tight fit is maintained between the fluid opening 46 of the dispensing key 40 and the opening 20 of the central bore 22 in the base of the adapter 2. The bottle of liquid anesthetic is elevated to cause a gravity forced stream of liquid anesthetic to flow through hose member 48 to be discharged via the fluid outlet 46A of the dispensing key 40, into the central bore 22 by way of the opening 20 in the floor of the guide channel 4. The liquid anesthetic continues to flow through the bore 22 into the interior of the anesthetic vaporizer canister by way of the lower opening 24 of the central bore 22. Once the vaporizer canister is full the retaining member 9 is turned to release the dispensing key 40 which is then removed from the guide channel 4. A sealing plug 56 is then inserted in the guide channel 4 to prevent evaporation of the anesthetic from the vaporizer canister.

If an attempt is made to refill a vaporizer canister 31A or 31B with the incorrect anesthetic, the selector 6 will ensure that either the fluid discharge opening 46A of the dispensing key 40 is harmlessly positioned against one of the interior walls of the guide channel 4, or the selector 6 will prevent the entry of the dispensing key 40 due to the placement of the detent 42. For example, if a refill key index 39 with a detent 42 configured in the manner illustrated in FIG. 5 is inserted in an adapter 2 configured with the selector 6 positioned for the detent 42 illustrated in FIG. 4 the discharge outlet 46A of the dispensing key 40 would be positioned against the roof of the guide channel 4. If an attempt is made to insert a refill key index 39 with the detent 42 configuration of FIG. 6 into an adapter 2 with the selector 6 positioned for the detent 42 illustrated in FIG. 5, the selector 6 would not match with the detent 42, thereby preventing entry of the dispensing key 40 of the refill key index 39 into the guide channel 4.

It must be emphasized that the configuration of the selector 6 of an adapter 2 and the configuration of the corresponding detent 42 of the refill key index 39 must be coordinated and dedicated to specific anesthetics. In combination with the anesthetic colour coding for vaporizers and refill bottles already in use, the refill key indexes, the adapter described herein will vertually eliminate inadvertant use of an incorrect anesthetic.

While particular embodiments of the invention have been illustrated and described, it will be understood that various changes and modifications can be made without departing from the spirit and scope of the invention and the invention should be limited only by the scope of the appended claims.

The embodiments of the invention in which an exclusive property or privilege is claimed are defined as follows:

1. Apparatus for use in refilling a standard anesthetic vaporizer canister having a threaded female fluid refill inlet, comprising:
    a body having an upper guide section provided with a male threaded base section means extending therefrom for removably securing in the re-fill inlet of the canister and an elongated passage extending through said guide section at an angle to said base section means and defining a tubular channel of a predetermined cross section extending through said guide section perpendicularly to said base section means, said channel having an aperture in the lower surface of said channel, duct means extending through said base means for fluidically communicating the aperture with the canister
    a coupling having inlet means at one end for fluidically communicating with a supply of liquid anesthetic and a dispensing key at its other end for connecting to said body, said dispensing key conforming in cross sectional size and shape to said tubular channel and being adapted to slide axially into said channel, said dispensing key having a fluid discharge outlet means in the lower surface thereof for fludically communicating said inlet means with the aperture in the lower surface of the channel;
    abuttment means extending into and located in said tubular channel for cooperative engagement with said dispensing key so as to limit the movement of said dispensing key in said channel to fix the fluid discharge outlet means of said dispensing key in alignment with the aperture in the lower surface of said channel only when a dispensing key so cooperatively configured is axially received in said channel.

2. The apparatus according to claim 1 including a plug having the shape of the dispensing key and being formed without a discharge outlet means adapted to be received in and to close said channel in the absence of a dispensing key.

3. The apparatus according to claim 1, wherein said abuttment means comprises at least one detent member projecting from at least one side surface of said channel into engagement with the leading end face of said dispensing key.

4. The apparatus according to claim 1, wherein said abuttment means comprises a predetermined corresponding array of recesses and detents formed on the surface of said dispensing key and channel, respectively.

5. The apparatus according to claim 1 including means for locking said dispensing key in said channel against axial movement.

6. The apparatus according to claim 5, wherein said locking means comprises screw means extending through said body into said channel.

7. The apparatus according to claim 1, wherein said dispensing key includes an air outlet in the lower surface thereof and said base section means of said body includes an air duct means therethrough for fludically communicating with the lower surface of said channel, said air outlet being located to be in fluid communication with said air duct means when said dispensing key is alinged in said channel and further including outlet means for fluidically communicating said air outlet with the supply of anesthetic.

8. The apparatus according to claim 7 including a groove formed in the lower surface of said channel adapted to be in fluid communication with said air outlet and said air duct means.

* * * * *